(12) United States Patent
Yeager et al.

(10) Patent No.: US 6,224,573 B1
(45) Date of Patent: May 1, 2001

(54) MEDICAMENT DISPENSER

(75) Inventors: James L. Yeager, Deerfield, IL (US); Joseph Y. Mo, Princeton, NJ (US)

(73) Assignee: NexMed Holdings, Inc., Robbinsville, NJ (US)

( * ) Notice: Subject to any disclaimer, the term of this patent is extended or adjusted under 35 U.S.C. 154(b) by 0 days.

(21) Appl. No.: 09/232,360

(22) Filed: Jan. 15, 1999

(51) Int. Cl.[7] .............. A61M 5/00; A61M 5/32; A61M 5/315; A61M 31/00
(52) U.S. Cl. .......... 604/181; 604/198; 604/218; 604/263; 604/275
(58) Field of Search .............. 604/93, 181, 187, 604/192, 198, 199, 218, 221, 263, 264, 275

(56) References Cited

U.S. PATENT DOCUMENTS

| | | | |
|---|---|---|---|
| 2,516,846 | 8/1950 | Betz | 128/264 |
| 2,518,486 | 8/1950 | Mende | 128/261 |
| 2,925,815 | 2/1960 | Lynn | 128/264 |
| 3,559,645 | * 2/1971 | Schaller | 128/216 |
| 4,469,482 | 9/1984 | Lissenburg et al. | 604/187 |
| 4,950,243 | 8/1990 | Estruch | 604/110 |
| 5,163,907 | 11/1992 | Szuszkiewicz | 604/110 |
| 5,531,703 | * 7/1996 | Skwarek et al. | 604/187 |
| 5,540,660 | * 7/1996 | Jenson | 604/110 |
| 5,833,382 | 11/1998 | Jenks et al. | 401/82 |
| 5,858,000 | * 1/1999 | Novacek et al. | 604/110 |

* cited by examiner

Primary Examiner—Richard K. Seidel
Assistant Examiner—Michael J. Hayes
(74) Attorney, Agent, or Firm—Olson & Hierl, Ltd.

(57) ABSTRACT

A disposable applicator for dispensing a desired quantity of a substantially non-runny medicant medicament, including a housing, a plunger and a replaceable cap. The housing is generally tubular having opposing proximal and distal ends and a tapered inner surface extending therebetween. The distal end terminates in a dispensing nozzle that defines a dispensing passageway in substantial coaxial alignment with the housing, while the inner surface has an alignment device. The plunger has a peripheral edge and is configured for axial movement within the housing, where the peripheral edge is aligned by the alignment device and slidingly guided by the inner surface, supporting the plunger therein. The plunger is configured for slidable advancement toward the dispensing opening by exertion of force by a user, so as to urge the medicament through the passageway.

5 Claims, 4 Drawing Sheets

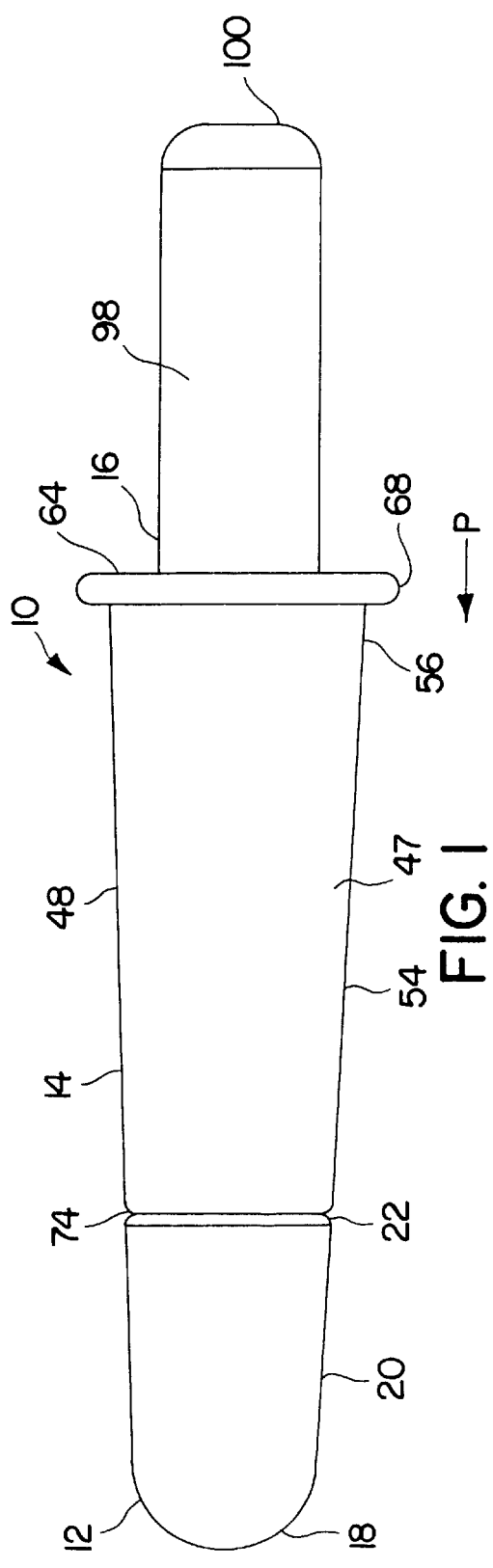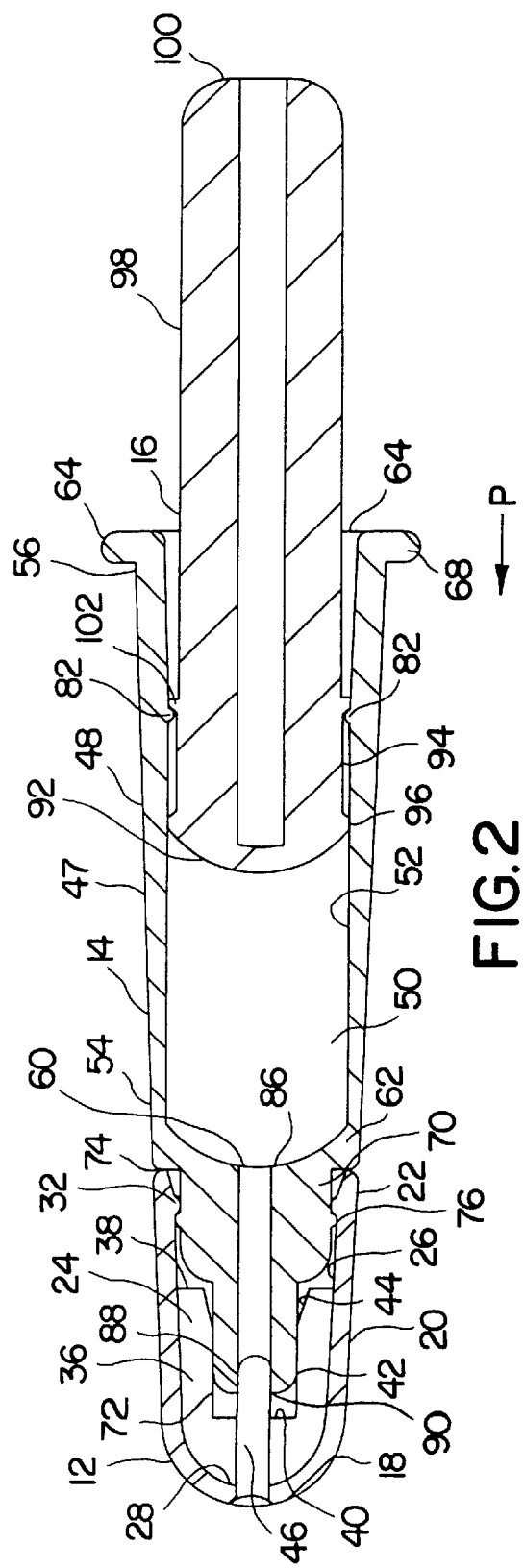

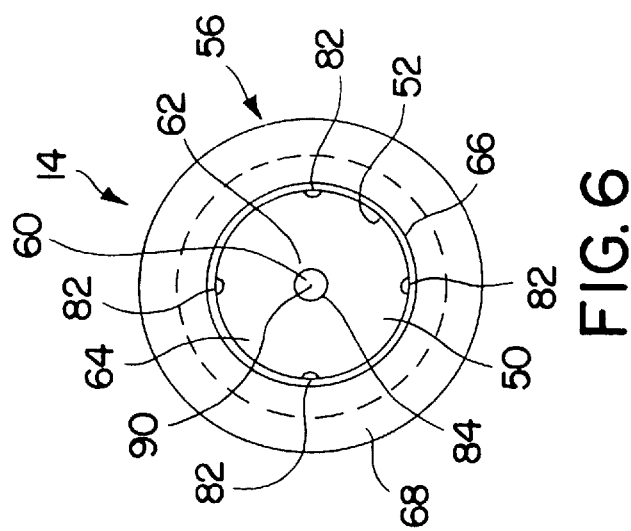
FIG. 6
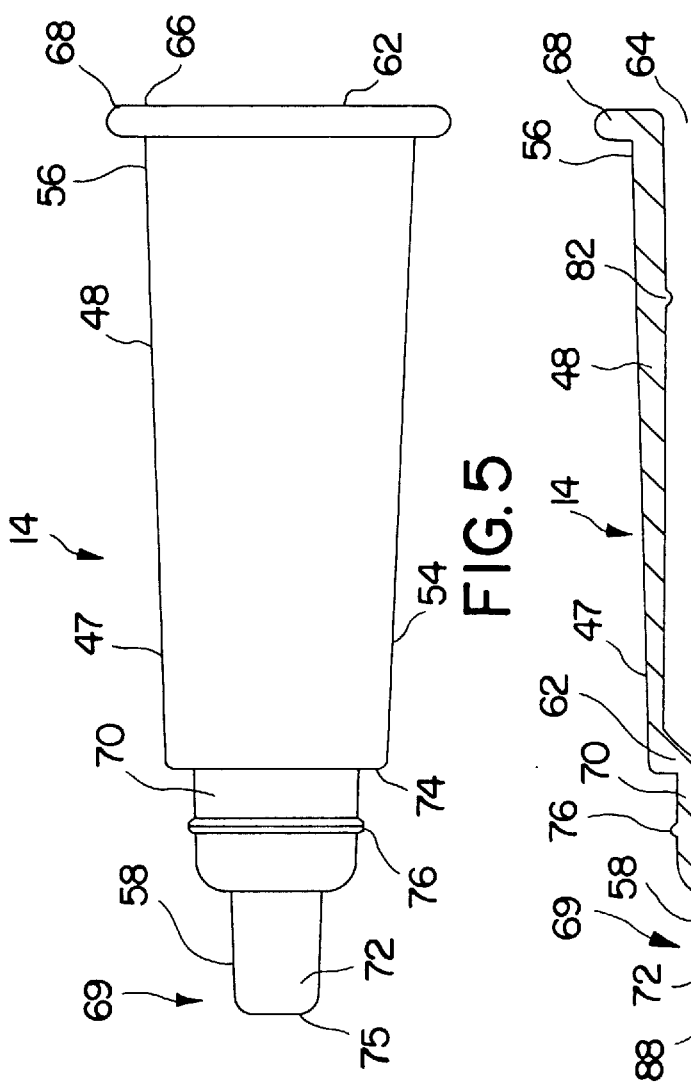
FIG. 5
FIG. 7
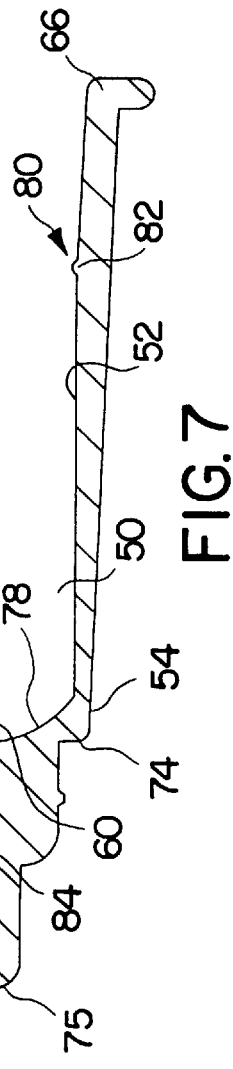

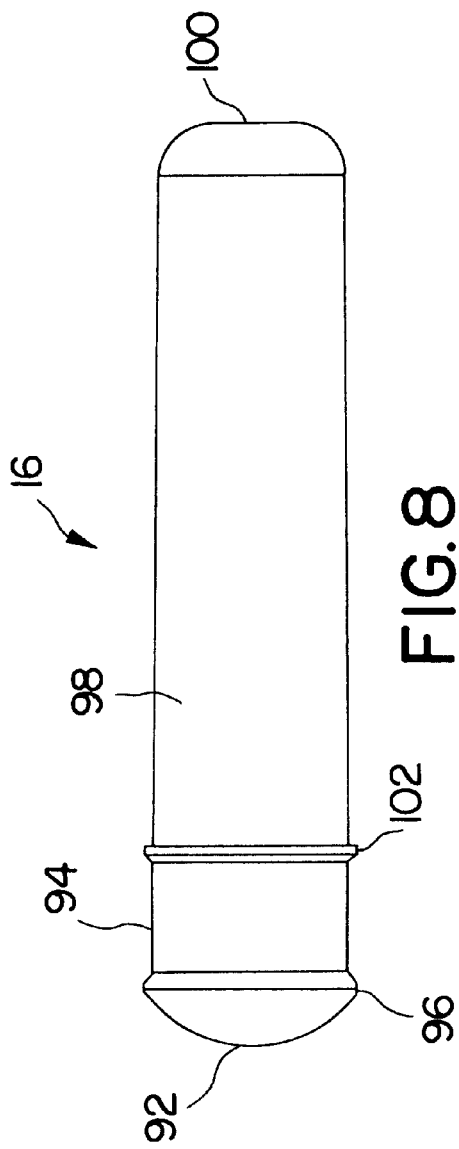
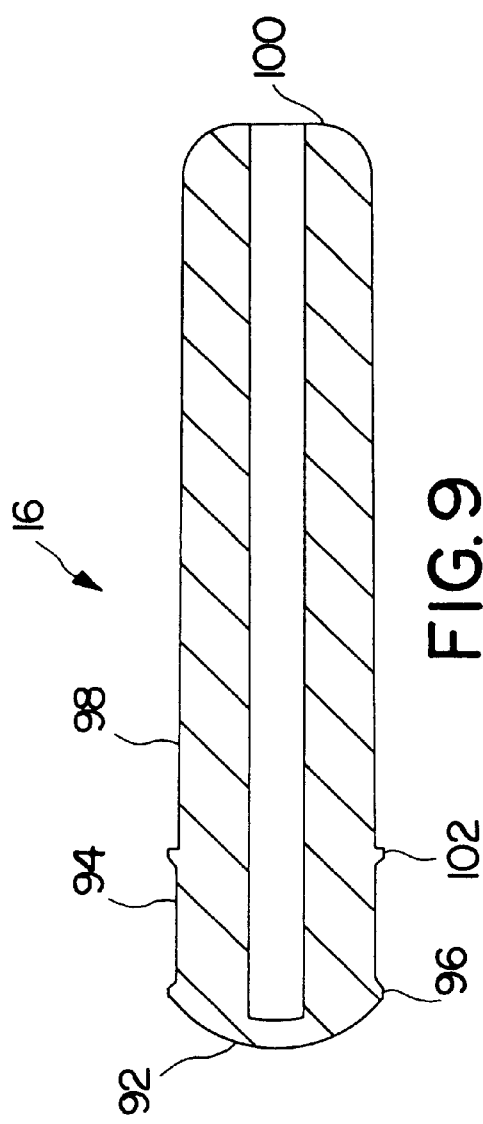

MEDICAMENT DISPENSER

TECHNICAL FIELD OF THE INVENTION

This invention relates generally to a container and applicator system. Specifically, this invention relates to a disposable dispensing container for dispensing a medicament to a targeted site.

BACKGROUND OF THE INVENTION

Heretofore it has been the practice to introduce substantially non-runny to semi-solid medicament materials, such as creams, ointments, gels, suspensions, solutions, colloids, salves and the like to a targeted site using a collapsible tube or jar with or without a dispenser. If a tube is utilized without a dispenser, the tube is squeezed by the user so that the medicant is forced out an opening onto the affected target area, generally bringing the tube in contact with the affected area. Use of a jar requires an applicator, or even the user's fingers, be "dipped" into the medicament prior to application.

Repeated use of the tube or jar can be messy, and subject the user to reinfection. Moreover, such tubes and jars are generally for topical use, and are not suitable for intraoral, intranasal, intra-aural, or intravaginal use.

Prior art attempts to alleviate these problems have included a dispenser, generally a tube, that is filled from the collapsible tube or jar. The dispenser is generally tapered and defined for body cavity introduction. However, repeated use of a non-disposable dispenser can cause reinfection in the user. Moreover, the combination of the collapsible tube or jar and dispenser is bulky and not readily disposable.

An alternate solution to the problems disclosed by the prior art have included syringes. However, while such syringes are readily used for introduction of the medicament into the body cavity, if reusable, the reinfection problem is not eliminated. If the syringe is disposable, the reinfection problem is eliminated, however syringes are difficult for nonmedical professionals to use, and may be intimidating. Furthermore, the plungers of the syringe are designed to be easily removable, and may cause loss of the material.

The present invention provides a device which overcomes the above-discussed problems using a disposable, applicator that doesn't leak, to provide a material to a targeted site.

SUMMARY OF THE INVENTION

The present invention provides a dispensing applicator suitable for use with a semi-solid medicament such as a cream, ointment, gel, suspension, viscous solution or colloidal suspension, salve, and the like. Moreover, the dispensing applicator provides for easy and accurate dosing of the medicament onto or into the body part at the site targeted for treatment, either as a single unit does or as several doses.

Examples of use of the dispensing applicator include delivery of a medicament to the urethra and urethral meatus for male erectile dysfunction; direct vaginal and/or clitoral application for female sexual dysfunction; intraoral application of a vaccine or oral care product; intranasal application of a vaccine or medicament; intra-aural application; or ophthalmic application of a medicament.

The disposable applicator includes a generally tubular hollow housing, a plunger and a replaceable cap. The housing includes opposing proximal and distal ends, a dispensing opening and a tapered inner surface with an alignment device. The distal end terminates in a dispensing nozzle which defines a dispensing passageway substantially co-axial with the housing. The plunger includes a peripheral edge and is configured for axial movement within the housing. The plunger peripheral edge is aligned by the alignment device and slidingly guided by the inner surface, supporting the plunger within the housing.

The replaceable cap is configured for engaging and covering the distal end of the housing in an airtight manner. Preferably, the airtight fit is provided by the interior surface of the replaceable cap engaging in a tight friction fit with the distal end of the housing. A plug on an interior surface of the cap operably engages and seals the dispensing opening and a first lip on the cap operably engages a lip on the housing.

Numerous other advantages and features of the present invention will become readily apparent from the following detailed description and from the accompanying drawings.

BRIEF DESCRIPTION OF THE DRAWINGS

In the drawings,

FIG. 1 is a elevational view of the dispensing container in accordance with the present invention, depicting the replaceable cap in a closed position and the plunger in a seated but undispensed position;

FIG. 2 is a transverse sectional view depicting the replaceable cap in a closed position with the dispensing container and the plunger in a seated but undispensed position;

FIG. 5 is a perspective view of the housing of FIG. 1 with the replaceable cap and plunger removed;

FIG. 6 is an end view of the housing of FIG. 5;

FIG. 7 is a transverse sectional view of the housing of FIG. 5;

FIG. 8 is a perspective view of the plunger of FIG. 1 removed from the housing; and FIG. 9 is a transverse sectional view of the plunger of FIG. 8.

DESCRIPTION OF THE PREFERRED EMBODIMENT

Figure 4:
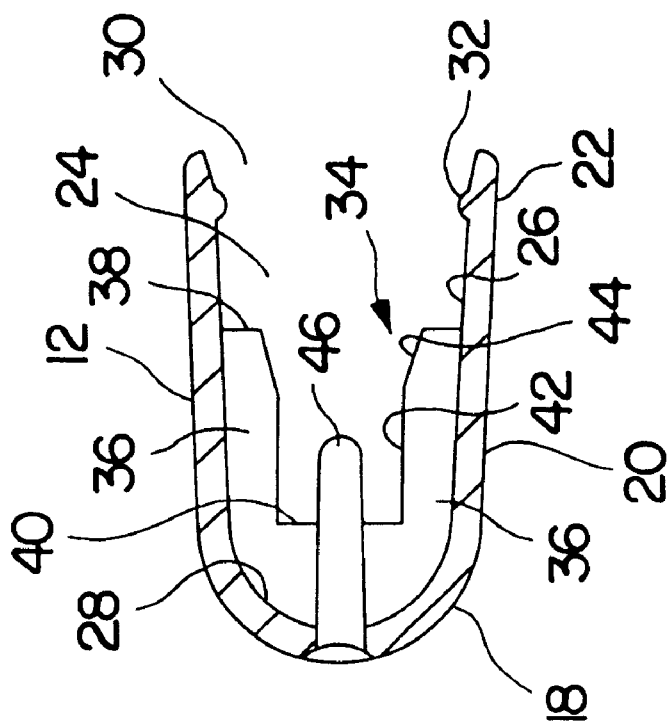
FIG. 4 is a transverse sectional view of the replaceable cap of FIG. 3.

Referring now to FIGS. 1 and 2, a dispensing container or applicator embodying the present invention is generally designated 10 and is constituted by a replaceable secure cap 12, a housing 14 and a plunger 16. Preferably, the dispensing applicator 10 is disposable and provides an application system for dispensing accurate doses of a medicament to a targeted site. Preferably the dispensing applicator 10 is a single-dose applicator; however, the applicator can be utilized for delivering more than one dose, if desired.

Desirably, the medicament is a substantially non-runny to semi-solid material, such as a cream, ointment, gel, suspension, viscous solution or colloidal suspension, salve, and the like. The dispensing applicator 10 provides for easy and accurate dosing of the medicament onto or into the exact site in need of treatment. Examples of use of the dispensing applicator 10 include delivery of the medicament to the urethra or urethral meatus for male erectile dysfunction; direct vaginal and/or clitoral application for female sexual dysfunction; intraoral application of a vaccine or oral care product; intra-aural delivery of medication; intranasal application of a vaccine or medicament; ophthalmic application of a medicament; as well as delivery to and around the anal orifice and the perianal region.

It is preferred that the dispensing applicator 10, i.e. the replaceable cap 12, housing 14 and a plunger 16, all be made of a rigid plastic material. A clear, translucent or opaque resin, such as polyolefin, e.g., polyethylene, polypropylene, and the like, suitable for injection molding is well suited for this purpose.

The replaceable cap 12 has an inverted cup-like shape when viewed from the side and a round shape when viewed from the end. Other configurations are contemplated, however, depending on the intended application. A generally domed lid 18 is included in the cap 12 with a skirt 20 depending therefrom. The skirt 20 further has a lower cap edge 22.

A chamber 24 is defined by an interior surface 26 (best seen in FIGS. 3 and 4) of the skirt 18 and a generally domed interior surface 28. Opposite the lid 18 is a lower opening 30. At least one contact point, a lip 32 (best seen in FIG. 3), projects generally radially inwardly from the interior surface 26, and extends around the inner circumference (interior surface) of the cap 12. While only one lip 32 is depicted, multiple lips can be provided if desired. Furthermore, instead of one lip 32 extending around the inner circumference of the cap 12, a plurality of generally radially inwardly extending nubs or the like spaced about the inner circumference can be utilized as well.

In a preferred embodiment, the skirt 18 is configured to have a tight friction fit with the housing 14, providing an air tight friction fit that prevents leaks. Upon closing the dispensing applicator 10, the replaceable cap 12 engages an upper end of the housing 14 and traps a volume of air therebetween to prevent weeping or leaking of the material.

Figure 3:
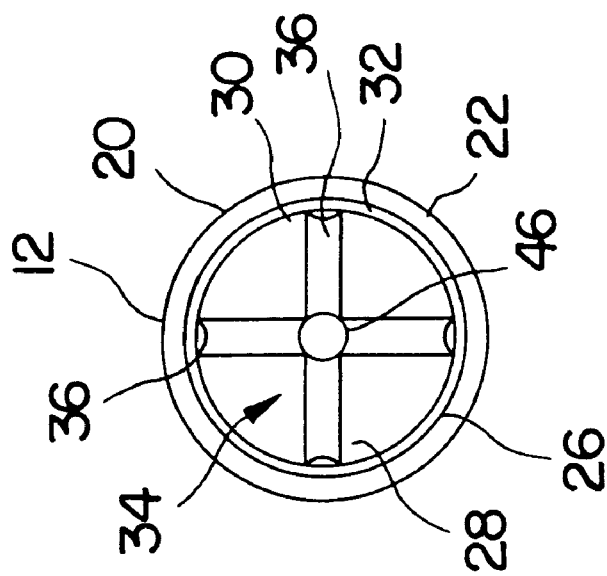
FIG. 3 is an end view of the cap of FIG. 1.

Turning now to FIGS. 3 and 4, the replaceable cap 12 is shown in greater detail. A seating device 34 is depicted, where seating device 34 ensures proper seating of the replaceable cap 12 on the housing 14 and provides an airtight fit with a distal end of the housing 14. In a preferred embodiment, seating device 34 includes at least one, but preferably two or more, upstanding members 36 projecting inwardly from domed interior surface 28 and interior surface 26, and spaced equally about the cap 12, forming a cross (best seen in FIG. 3).

It is preferred that each upstanding member 36 include a first and second flat portion or land 38 and 40, and a longitudinal portion 42 having an angled guiding portion 44 (best seen in FIG. 4). Each first flat portion 38 and angled guiding portion 44 act in concert to ensure proper seating of the replaceable cap 12, while correspondingly, each longitudinal portion 42 ensures a airtight fit with the distal end of the housing 14.

FIGS. 3 and 4 illustrate that the airtight fit of the replaceable cap 12 further comprises at least one longitudinal plug 46 formed on the domed interior surface 28 and extending inwardly therefrom, i.e., into the chamber 24. Plug 46 operably engages and seals at least one dispensing opening formed in the distal end of the housing 14. This operable engagement not only ensures proper seating of the cap 12, but provides an airtight fit, preventing weeping or leaking of the material.

Referring to FIGS. 5–7, the housing 14 has a generally tubular shape, and is configured for dispensing a predetermined dose of the medicament. Although the generally tubular shape and use of a relatively rigid plastic is preferred, other configurations and materials can be utilized depending on the application. The housing 14 has a barrel portion 47 which includes a generally tapered tubular wall 48 defining a housing chamber 50 via a tapered inner surface 52. Housing 14 further includes an outer surface 54, a proximal end 56, and a distal end 58 opposite the proximal end 56.

Tubular wall 48 preferably has two openings, an upper opening 60 defined by an upper end 62, and a lower opening 64 defined by lower end 66. While two openings are preferred, three or more are contemplated. In the preferred embodiment, upper and lower openings 60 and 64 are longitudinally aligned and in fluid communication with the housing chamber 50. As readily apparent from FIGS. 6 and 7, lower opening 64 has a greater inner circumference than the housing chamber 50, which in turn has a greater inner circumference than the upper opening 60. This arrangement allows for the tapered inner surface 52 and facilitates the automated filling operation of housing 14 and seating of the plunger 16.

A concentric ring 68 is shown, formed on the outer surface 54 at lower end 66 and extending generally radially therefrom. Ideally, the concentric ring 68 is integral with the housing 14 and is utilized by the user to secure the dispensing applicator 10 when pressure is applied to the plunger 16. While one concentric ring 68 is shown, other holding and securing expedients can be utilized, including at least two members extending from and spaced about housing 14.

As depicted in FIGS. 5 & 7, distal end 58 is tapered in a stepped fashion and terminates in a nozzle 69, having an engaging portion 70 and a smooth rounded tip 72 for placement directly on the targeted site. In the preferred embodiment, barrel portion 47, engaging portion 70 and tip 72 are integral, formed as one piece during the injection molding process. However, these pieces can be formed separately and joined together by bonding or the like. Further, as shown, barrel portion 47 defines a shoulder 74 at upper end 62 having a larger outer circumference than the engaging portion 70, which in turn has a larger outer circumference than the tip 72.

Tip 72, including smooth rounded end 75, is between about 4 mm and about 6 mm in length, preferably about 5 mm, and is provided for direct placement on or in the target site of need. Tip 72, and nozzle 69, are designed to prevent injury or discomfort when it contacts the body surface, and is of sufficient length for easy and accurate application of the medicament material directly onto or into the body part at the exact site of need.

The nozzle 69 is suitable for delivering the medicament directly onto or into the body, including the urethra, the vagina, the ear and the eye, to name but a few body parts. The tip 72 and nozzle 69 provide easy access into and around these body parts, while the shoulder 74 inhibits penetration, and minimizes the likelihood of injury to the surrounding tissue. For example, the tip 72 and the nozzle 69 provide easy access into the ear, while the shoulder 74 prevents the tip 72 and nozzle 69 from penetrating the ear beyond a safe, predetermined depth.

In the illustrated embodiment, engaging portion 70 includes a second contact point, at least one lip 76 (best seen in FIGS. 5 & 7), projecting generally radially outwardly from the engaging portion 70, and extending around the outer circumference thereof. While only one lip 76 is depicted, multiple lips can be provided. Furthermore, instead of one lip 76 extending around the outer circumference of the engaging portion 70, a plurality of generally radially outwardly extending nubs spaced about the engaging portion 70 can be provided.

Dispensing chamber or passageway 84, having opposing first and second ends 86 and 88, is formed in the housing 14, substantially coaxially aligned with the housing chamber 50 where first end 86 is in fluid communication with upper opening 60. Correspondingly, second end 88 is in fluid communication with at least one dispensing opening 90.

While one dispensing chamber and opening 84 and 90 are depicted, multiple openings and chambers 90 and 84 are contemplated, depending on the material and application. Furthermore, the dispensing opening and chamber 90 and 84 have an inner circumference slightly larger than the outer circumference of the plug 46, providing a liquid tight friction fit therebetween. When cap 12 is properly placed on the housing 14, plug 46 operably engages the dispensing opening and chamber 90 and 84, securing the dispensing opening 90 to prevent leaks. While the dispensing opening 90 and chamber 84 are depicted as having the same circumference, this relationship can differ. For example, the dispensing chamber or passageway 84 can have a larger inner circumference than the dispensing opening 90.

Replaceable cap 12 is secured to the housing 14 by the respective contact points formed thereon, which work to form an airtight snap fit when the replaceable cap 12 is placed on the housing 14. Specifically, the lip 32, extending inwardly from the cap 12, operably engages the lip 76 extending outwardly from the engaging portion 70, forming an airtight snap fit that secures the replaceable cap 12 to the housing 14 (best seen in FIG. 2). When replaceable cap 12 is properly placed and secured to the housing 14, lower end 22 abuts against shoulder 74, which prevents the material from leaking from the cap 12.

In addition to the contact points, the seating device 34 also acts to properly place and secure the replaceable cap 12 on the housing 14. The inner circumference of the replaceable cap 12, measured between the longitudinal portions 42 of at least two opposing upstanding members 36 is slightly larger than the outer circumference of the tip 72, forming an airtight friction fit therebetween. The angled guided portions 44 are used to properly align the tip 72 in the replaceable cap 12, while the longitudinal portions 42 provide the airtight friction fit therebetween.

A rounded top chamber 78 in housing 14 is defined by inner surface 52 at upper end 62. Additionally, an alignment device 80 is formed on the inner surface 52, where the alignment device 80 aligns the plunger 16 within the housing chamber 50 in addition to preventing accidental removal thereof. Specifically, the alignment device 80 comprises at least one nub 82 formed part way along the inner surface 50, spaced a predetermined distance from lower end 66. In the preferred embodiment, the alignment device 80 comprises four nubs 82 unitary with and projecting radially inwardly from the inner surface 52. The four nubs 82 are spaced equally about the periphery of inner surface 52 to provide for accurate and tight placement of the plunger 16 after the housing chamber 50 is filled with the medicament material.

Another important feature of the present invention is the platform 16 mounted for axial movement within the housing 14 as detailed in FIGS. 8 & 9. Preferably made of molded plastic like a polyolefin, the plunger 16 has a generally tubular shape when viewed from the side, and like the cap 12, has a generally round shape when viewed from the end. Other shapes of plunger 16 can be used depending on the shape of the housing 14. The platform 16 preferably includes a generally domed upper surface 92 that supports the material within the housing 14, with a skirt 94 depending from a peripheral edge 96 of the upper surface 92.

Housing chamber 50 is filled with the medicament by an automatic filling process. This process is facilitated by tapering the inner surface 50. When filled, the dispensing applicator 10 is assembled by inserting the upper surface 92 of the plunger 14 into housing chamber 50, where the alignment device 80 ensures proper alignment of the plunger 14. Specifically, plunger 16 is accurately aligned, and tight placement is assured, by the peripheral edge 96 operably engaging the plurality of nubs 82.

When assembled, housing chamber 50 is further defined by inner surface 50, rounded domed upper surface 92 and rounded top chamber 78. In the preferred embodiment, the peripheral edge 96 is slidingly guided by the inner surface 50 of the housing 14, with preferably sufficient frictional engagement to support the plunger 16 at a desired position within the housing 14. The plunger 16 is further configured for slidably advancing towards the rounded top chamber 78 and the dispensing opening 90 in a direction indicated by the arrow P (best seen in FIG. 2) by exertion of a force by a user. Preferably, the user's thumb presses against the outer surface 98 or a generally flattened pushing end 100. In this manner, the medicament is dispensed through the dispensing chamber or passageway 84 and the nozzle opening 90.

The embodiment depicted in FIGS. 2, 8 and 9 reveals that at least one concentric ring 102 is provided on the plunger 16 spaced a predetermined distance from the peripheral edge 96. In a preferred embodiment, at least one concentric ring 102 is unitary with and extends generally radially from the plunger 16. Moreover, while the concentric ring 102 is depicted, a plurality of spaced rings 102 can be provided.

The concentric ring 102 performs a number of functions. The ring 102 forms a tight friction fit with inner surface 52 and is slidingly guided thereby. This tight friction fit provides for proper seating of the plunger 16 during automated filling operation and ensures the airtight integrity of the housing 14, when housing 14 is filled with material.

Additionally, the concentric ring 102 prevents accidental removal of the plunger 16 and loss of the medicament confined within the chamber 50. When plunger 16 is properly seated in the housing chamber 50 of the housing 14, concentric ring 102 operably engages the nubs 82 formed on inner surface 52. Such operable engagement not only ensures proper seating of the plunger 16, but prevents the plunger 16 from being pulled out of the housing 14 and losing material.

As apparent from the drawings, plunger 16, including domed upper surface 92 and peripheral edge 96, tightly fits within the housing chamber 50 and is slidingly guided by the inner surface 52, supporting the plunger 16 within the housing 14. This tight fit facilitates the substantially complete dispensing of the material from the housing chamber 50. Peripheral edge 96 and domed upper surface 92 scrap the material from the inner surface 52 as the plunger 16 is advanced. Additionally, domed upper surface 92 tightly fits inside rounded top chamber 78 when plunger 16 is fully depressed. This arrangement provides for delivery of a maximum net dose and results in minimal material retained in the housing 14 when plunger 16 is advanced.

An objective of the applicator 10 is that the material be prevented from leaking past plunger 16 onto the user's hands or to a shelf or other substrate upon which the dispensing applicator 10 rests when not in use. This sealing engagement is preferably accomplished by the domed upper surface 92, peripheral edge 96 and concentric ring 102 having an air tight friction fit with inner surface 52 of housing 14.

Referring now to FIG. 2, the manner in which the subject applicator 10 operates is shown in greater detail. The user grips the applicator 10, generally around housing 14, abutting concentric ring 68. A force is applied to the domed upper surface 92 by the user by manually urging the generally flattened pushing end 100, or alternately outer surface 98, towards the upper end 62 of the housing 14 (in the direction of arrow P). The upper surface 92 urges the medicament through the dispensing opening 90, thus delivering a single, predetermined dose of the material. For dispensing more than one dose seriation appropriate markings can be provided on housing 14.

The applicator 10 may contain more than one dose, if desired. After the desired quantity of the material has been dispensed, the user ceases to push against the plunger 16.

Referring now to FIG. 2, the replaceable cap 12 is depicted in a closed relationship with housing 14. The replaceable cap 12 engages the housing 14 and covers the nozzle 69, including the tip 72, in an air tight manner as set forth above, and thus traps a volume of air when closing or engaging the housing 14. After the desired amount of the material is dispensed, the user places the replaceable cap 12 on the housing 14. In addition to the ability of the plunger 16 to recede away from the upper end 62 to relieve residual stress, the volume of air trapped in the replaceable cap 12 has been found to further push the material, and the plunger 16, away from the dispensing opening 90 and back towards the lower opening 64. The use of the cap 12 in this manner reduces the potential for leakage of material. As such, unwanted weeping and creeping is prevented.

The present invention is not limited to the number, configuration, angular orientation, method of joining and/or spacing of the cap 12, housing 14, and plunger 16. Preferably dispensing applicator 10, i.e. the replaceable cap 12, housing 14 and a plunger 16, are all be made of a rigid plastic material of clear, translucent or opaque resin, such as a polyolefin, e.g. polyethylene, polypropylene, and the like, suitable for injection molding However, other materials and methods for manufacturing and assembling the applicator 10 including molding individuals parts and assembly those parts by chemical adhesives and/or ultrasonic welding.

While a particular embodiment of the present dispenser has been shown and described, it will be appreciated by those skilled in the art that changes and modifications may be made thereto without departing from the invention its broad aspects and as set forth in the following claims.

We claim:

1. A disposable applicator for dispensing a medicament and a medicament contained therein, the combination comprising:

a generally tubular hollow housing having opposing proximal and distal ends and a tapered inner surface extending therebetween, said distal end terminating in a dispensing nozzle defining a dispensing passageway substantially in coaxial alignment with the housing, and said inner surface having an alignment device and defining a rounded top chamber adjacent said distal end;

a plunger having a dome shaped distal end and a peripheral edge and configured for axial movement within said housing, said peripheral edge being aligned by said alignment device and slidingly guided by said inner surface for supporting said plunger within said housing, said plunger configured for slidable advancement toward said dispensing passageway by exertion of force by a user into a relationship wherein said dome shaped distal end fits inside said rounded top chamber of said housing, said force urging the medicament through said passageway; and a medicament contained in said housing.

2. The container of claim 1 further comprising a replaceable cap configured for engaging and covering said distal end, said cap having an airtight fit with said distal end of said housing.

3. The container of claim 2 wherein said dispensing nozzle includes a tip suitable for insertion into a body opening such as a urethra.

4. The container of claim 3 wherein said tip has a predetermined length and includes a smooth rounded end, whereby said smooth rounded end is placed in direct contact with a surface to which the medicament is to be applied.

5. The container of claim 4 wherein said smooth rounded end includes at least one dispensing opening in fluid communication with said dispensing passageway, whereby said medicament is applied to said surface.

* * * * *